United States Patent [19]

Taylor

[11] Patent Number: 5,279,564
[45] Date of Patent: Jan. 18, 1994

[54] CANNULA RETENTION DEVICE

[75] Inventor: Warren Taylor, Cary, N.C.

[73] Assignee: Edward Weck Incorporated, Research Triangle Park, N.C.

[21] Appl. No.: 943,785

[22] Filed: Sep. 11, 1992

[51] Int. Cl.$^5$ .................. A61M 25/04; A61M 29/00
[52] U.S. Cl. ................................ 604/104; 606/198
[58] Field of Search .............. 604/105-108; 164, 174, 178, 606/198

[56] References Cited

U.S. PATENT DOCUMENTS

| 365,969 | 7/1887 | Collins | 604/105 |
|---|---|---|---|
| 1,621,159 | 3/1927 | Evans . | |
| 3,039,468 | 6/1962 | Price . | |
| 3,261,357 | 7/1966 | Roberts et al. . | |
| 3,713,447 | 1/1973 | Adair . | |
| 3,717,151 | 2/1973 | Collett . | |
| 3,774,596 | 11/1973 | Cook . | |
| 3,882,852 | 5/1975 | Sinnreich . | |
| 4,198,981 | 4/1980 | Sinnreich . | |
| 4,244,033 | 12/1980 | Bordow . | |
| 4,250,873 | 2/1981 | Bonnet . | |
| 4,608,965 | 9/1986 | Anspach et al. . | |
| 4,699,611 | 10/1987 | Bowden . | |
| 4,861,334 | 8/1989 | Nawaz . | |
| 4,995,868 | 2/1991 | Brazier . | |
| 5,053,009 | 10/1991 | Herzberg . | |
| 5,112,321 | 5/1992 | Hiltebrandt | 604/264 |
| 5,163,949 | 11/1992 | Bonutti | 604/192 |
| 5,183,465 | 2/1993 | Xanthakos | 604/108 |

FOREIGN PATENT DOCUMENTS

| 0368473 | 5/1990 | European Pat. Off. . |
|---|---|---|
| 0432363A2 | 6/1991 | European Pat. Off. . |
| 640126 | 10/1936 | Fed. Rep. of Germany . |
| 647326 | 6/1937 | Fed. Rep. of Germany . |
| 2238508 | 2/1973 | Fed. Rep. of Germany . |
| 4021153A1 | 1/1992 | Fed. Rep. of Germany . |
| 748666 | 7/1933 | France . |
| 11277 | 1/1908 | United Kingdom . |

OTHER PUBLICATIONS

"The Gazayerli Endoscopic Retractor Model 1", M. M. Gazayerli, Brief Clinical Report.

Primary Examiner—Jerome L. Kruter
Attorney, Agent, or Firm—Rosenblatt & Associates

[57] ABSTRACT

The invention relates to a cannula with a fixation mechanism actuable to secure the cannula above and below the body wall with minimal amount of manipulation and damage to the body wall. The preferred embodiment involves arms attached to springs secured to the body of the cannula over which a sleeve is slidingly mounted to restrain and release the springs. When the spring is released, it causes the arms to press against the inner body wall to fixate the cannula. A stop mounted on the sleeve can be positioned to apply a compressive force on the outer body wall, further securing the cannula.

22 Claims, 2 Drawing Sheets

CANNULA RETENTION DEVICE

FIELD OF THE INVENTION

This invention relates to medical instruments such as cannulas and ways to secure them to a body opening.

BACKGROUND OF THE INVENTION

In laparoscopic surgery, access to the surgical site is gained by small a incision in the body wall through which cannulas are passed. The cannula is essentially a tube equipped with a valve to prevent loss of gas which has been used to inflate the body cavity. Various instruments are inserted into the body cavity through the cannula. One or more cannulas can be used during a procedure, and sometimes as many as four or six can be used during a given procedure. During the procedure, the surgeon manipulates the instruments in the cannulas, sometimes using more than one instrument at a time.

The action of the surgeon in manipulating the instruments causes frictional forces between the instrument and the cannula valve, which results in cannula movement responsive to movements of the instruments by the surgeon's hand. The potential exists for the cannula slipping out of the body wall, which causes a loss of pneumoperitoneum. This situation creates difficulty of reinserting the cannula and delays the procedure.

In the past, cannulas have been attached to the body wall by separate mechanisms. One mechanism engages the underside of the body wall to prevent cannula pullout. The other mechanism is put in place outside the body wall to prevent the cannula from being pushed in. These separately actuable mechanisms for securing the cannula against pull out or push in present problems in reliability of engagement to the body wall and difficulty in obtaining the necessary fixation of the cannula to the body wall. Several prior designs have involved toggle bolt-type operation, which has resulted in needless tissue trauma in the area inside the body wall, and a cumbersome procedure to engage the cannula.

In the past, various mechanisms have been used to secure placement of a variety medical devices. Some have employed a sliding sleeve technique which, upon longitudinal movement, causes a flexible member to bend outwardly adjacent the distal end of the instrument. Toward the proximal end, a flange or other mechanical means are employed so that the flexible member and the flange help to retain the instrument. Typical of such devices are U.S. Pat. No. 3,713,447; German Patent No. 2238508 (German equivalent of U.S. Pat. No. 3,713,447); German Patent No. 4021153A1 (mechanical linkage at distal end); European Patent No. 0432363A2; European Patent No. 0368473 and its U.S. equivalent, U.S. Pat. No. 4,995,868. Yet, other fixating mechanisms for insertable instruments into the body have featured a toggle-type mechanism at the distal end of the instrument to fixate it within the body wall. Typical of such devices are the Gazayerli Endoscopic Retractor Model 1 which has a toggle assembly at the distal end. Also along this line is German Patent No. 640126, which has alternative embodiments of a toggle arrangement that recedes into a sleeve, as well as a flexible member that can be expanded from the proximal end of the instrument. French Patent No. 748666 has pivoting members that flip up upon the shifting of a sleeve to retain the trocar to the inside of the body opening. Other toggle-type arrangements at the distal end are shown in British Patent No. 11277; U.S. Pat. Nos. 4,608,695; 3,261,357; and 3,039,468. Other devices employ longitudinal cutouts in a sleeve member, making its distal end flexible when subjected to a compressive force. The radial expansion assists in positioning of the instrument. Typical of such devices are U.S. Pat. Nos. 5,053,009; 1,621,159; 4,250,873; and 4,699,611. German Patent Nos. 647326 and 641240 again illustrate flexible sleeves expanding radially outwardly at the distal end of the instrument under a compressive force to assist in holding the position of the instrument. U.S. Pat. No. 3,717,151 has a plurality of fingers which are biased radially outwardly to prevent pullout of a flesh-penetrating apparatus. U.S. Pat. No. 4,861,334 uses a balloon to hold the position of a gastronomy tube. Other patents illustrating the use of inflatable means to either assist in retaining the position of an instrument or for other purposes are U.S. Pat. Nos. 4,244,033 and 4,198,981.

What has been lacking in prior designs is a simple-to-use and simple-to-build reliable mechanism for fixating the cannula with respect to the body wall. Another feature which is desirable and not present in the prior designs is a simple-to-control fixating mechanism which requires minimal manipulation to deploy, decreasing the possibility of damaging body tissue. Further, it is desirable to have a device which is sensitive to the surrounding tissue and the body wall, yet, at the same time, acts closely inside and outside the body wall to firmly and securely hold the cannula in the desired position as the procedure progresses. Also, it is desirable to have a device which is adjustable to a range of body wall thicknesses. Those, and other, advantages of the invention will be described below.

SUMMARY OF THE INVENTION

The invention relates to a cannula with a fixation mechanism actuable to secure the cannula above and below the body wall with minimal amount of manipulation and damage to the body wall. The preferred embodiment involves arms attached to springs secured to the body of the cannula over which a sleeve is slidingly mounted to restrain and release the springs. When the spring is released, it causes the arms to press against the inner body wall to fixate the cannula. A stop mounted on the sleeve can be positioned to apply a compressive force on the outer body wall, further securing the cannula.

DETAILED DESCRIPTION OF THE PREFERRED EMBODIMENT

Figure 2:
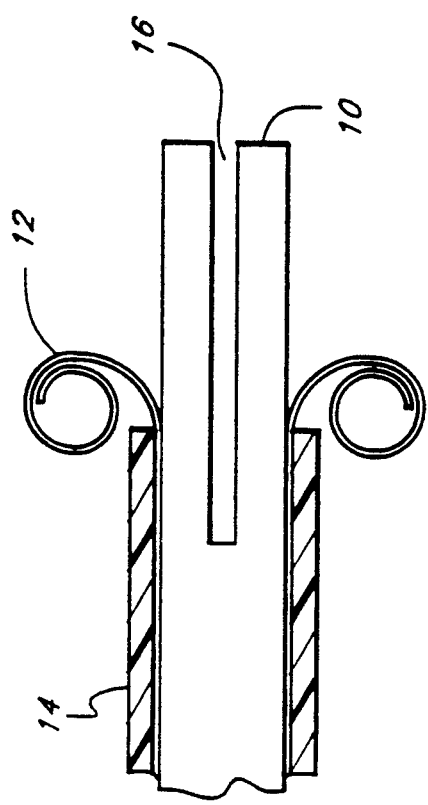
FIG. 2 shows the cannula with spiral springs in unrestrained position.
Figure 3:
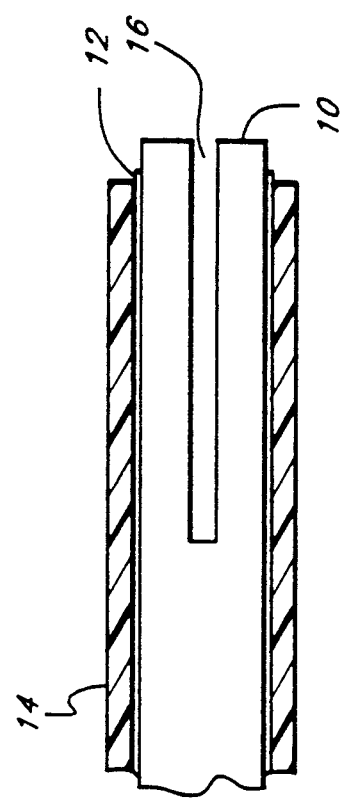
FIG. 3 shows the view of FIG. 2 with the spiral springs being restrained against the cannula body by the sleeve.
Figure 1:
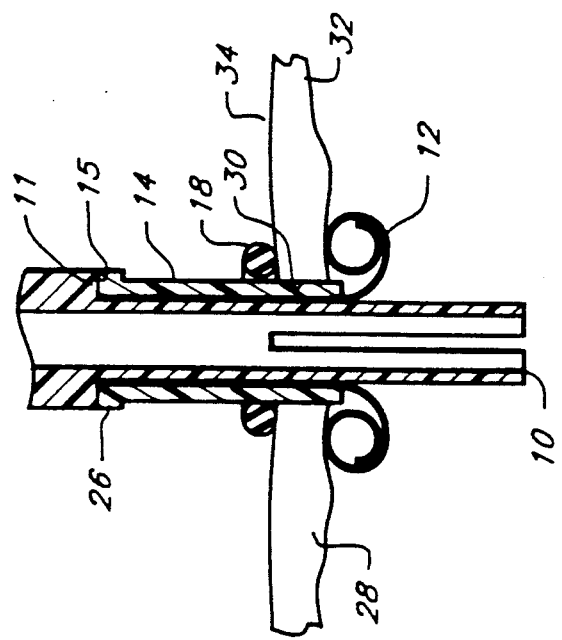
FIG. 1 shows the spiral springs in unrestrained position while the cannula is in place through an opening in the body wall.

The apparatus A is shown in FIG. 1. A cannula 10, having a shoulder 11 on its proximal end, is shown with a plurality of shape-memory elements 12 attached to the cannula 10. The elements 12 are biased to expand outwardly when unrestrained (see FIG. 2). A sleeve 14 circumscribes the cannula 10. The sleeve 14 slides longitudinally along the cannula 10. A stop 18 circumscribes sleeve 14. Typically, stop 18 is an O-ring. As shown in FIG. 3, when the sleeve 14 is fully extended, it is located adjacent the elements 12 which are restrained against the cannula 10. When restrained in this position, the elements 12 store potential energy. As the sleeve 14 is retracted longitudinally along the cannula 10, the elements 12 are gradually rendered unrestrained, thereby changing their stored energy to kinetic energy. To facilitate operation, sleeve 14 has a knob 26, which can be gripped by the surgeon during the fixation of the cannula 10. Referring again to FIG. 1, the elements 12 are attached adjacent the proximal end 15 of the cannula 10 and, when restrained, ride in slots 16 on the body of the cannula 10. Those skilled in the art will understand that the slots act as recesses for the elements 12, allowing the outer diameter of the apparatus to be minimized. The manner of securing the elements 12 to the cannula 10 can take many forms, such as adhesive or fasteners. By way of illustration only, and not intending to limit the scope of the invention, the elements 12 may be coiled springs. Further, the number of elements 12 may vary depending on the individual requirements of each apparatus, for example, incision size, retention force required, or sensitivity of surrounding body tissue.

FIG. 1 shows the apparatus deployed through an incision 30. When unrestrained, the springs 12 coil or roll up along the body of the cannula towards its proximal end 15. The springs 12 continue to coil in this manner until contact is made with the inner body wall 32 against which the springs apply a compressive force, securing cannula 10 in the incision 30. Those skilled in the art will understand elastic elements employed in this fashion allow cannula 10 to adapt to individual body wall thickness.

Stop 18 can be moved adjacent the outer body wall 34 to apply an inward compressive force, to further secure cannula 10 in the incision 30. The sleeve 14, when fully retracted, abuts shoulder 11, preventing cannula 10 from being pulled further into the incision by the force of the springs. Those skilled in the art will also understand that when sleeve 14 is fully retracted, i.e. adjacent the proximal end 15 of cannula 10 and abutting shoulder 11, it should extend through the incision in the body wall. This configuration lessens damage to body tissue when sleeve 14 is retracted and extended along cannula 10.

Figure 6:
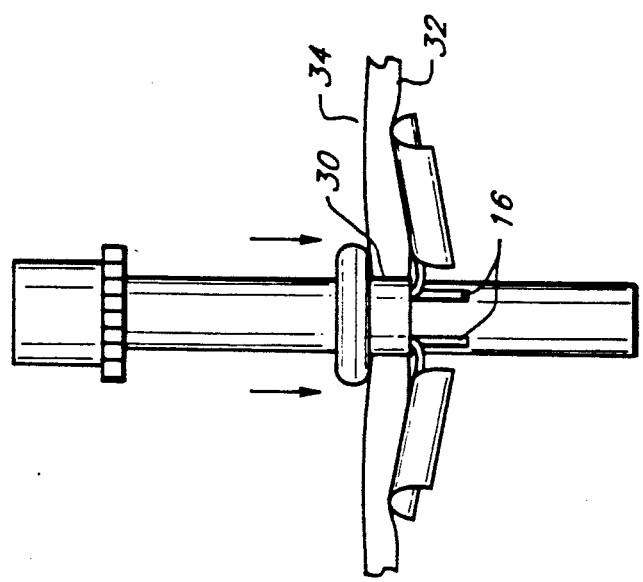
FIG. 6 is the view of FIG. 4 showing the springs in unrestrained position, allowing the arms to push against the inner body wall while the cannula is in place through an opening in the body wall.
Figure 5:
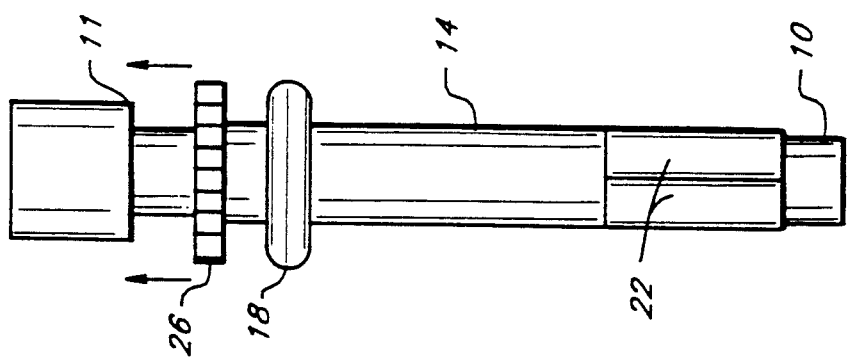
FIG. 5 shows the view of FIG. 4 with the springs being restrained by the sleeve against the cannula body and the arms flush with the sleeve.
Figure 4:
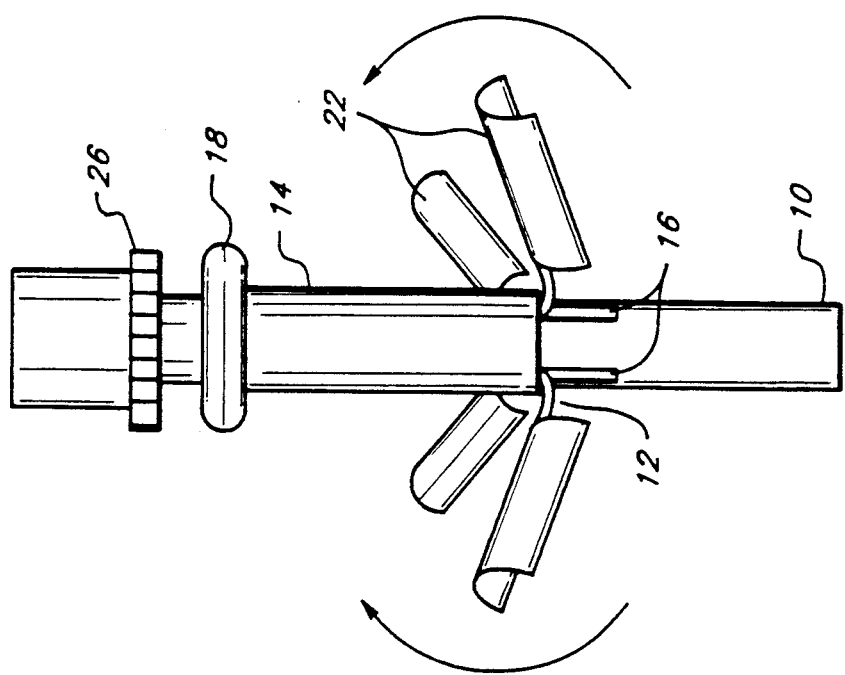
FIG. 4 shows the cannula with arms attached to the unrestrained springs.

The preferred embodiment is illustrated in FIGS. 4, 5, and 6. In the preferred embodiment, arms 22 are used to distribute the compressive load applied by the apparatus, thus avoiding tissue damage which could be created by point loads applied to the body wall. Each arm 22 is attached to an element 12 and distributes the compressive force created by its element 12 over a larger tissue area than does the element 12 when it is in direct contact with the tissue. Thus, the arms 22 function to decrease possible damage to the body tissue. In the preferred embodiment, the arms 22 are intended to fit flush with sleeve 14 and circumscribe cannula 10. This further reduces tissue damage upon insertion and extraction of the apparatus. A flush fit can be achieved by constructing each arm of curved material having the same outer radius as sleeve 14. For example, if the apparatus has four arms, each arm could be constructed of quarter round tubing having the same outer radius as sleeve 14. As shown in FIG. 5, when sleeve 14 is positioned to constrain elements 12, the arms 22 encase a portion of the distal end of cannula 10 and fit flush with the outer surface of the sleeve. Again, slots 16 can be used to reduce the outer diameter of the apparatus.

The fixation of the cannula 10 is shown in FIG. 6. Cannula 10 is inserted through an incision 30 in the body wall. Thereafter, the surgeon grabs knob 26 on sleeve 14 and retracts the sleeve by applying an extractive force until sleeve 14 abuts shoulder 11. The retraction releases the potential energy stored in the elements 12, resulting in an outward expansion of elements 12. As elements 12 expand outward, the arms 22 push against the inner body wall 32, resulting in fixation of cannula 10. Stop 18 is adjusted on sleeve 14 to a position which seals the joint between the incision 30 and the apparatus. When adjusted to this position, stop 18 also further inhibits movement of the apparatus. Because it is desirable to limit movement of the apparatus once it is inserted in the incision, stop 18 can be an O-ring. The O-ring is positioned by rolling, as opposed to pushing, it along the surface of sleeve 14. This reduces unnecessary pushing and pulling of the apparatus, thus preventing further damage to the tissue surrounding the incision.

Those skilled in the art will appreciate other forms of execution of sleeve 14 and stop 18 can be employed without departing from the spirit of the invention. For example, stop 18 and sleeve 14 can have mating threads in which case stop 18 is rotated into position.

In another embodiment, cannula 10 and sleeve 14 can have mating threads. Therefore, instead of sliding sleeve 14 over cannula 10 to extend and retract sleeve 14, it is rotated. Further, this configuration renders the depth of the cannula 10 in the incision adjustable.

The elastic elements 12 can be made of any material which retains its shape when unrestrained, for example, nitinol or a super elastic spring metal. The cannula 10, sleeve 14, and arms 22 can be made from the same material. Preferably, a thermoplastic material can be used.

The foregoing disclosure and description of the invention are illustrative and explanatory thereof, and various changes in the size, shape and materials, as well as in the details of the illustrated construction, may be made without departing from the spirit of the invention.

I claim:

1. A fixation apparatus to hold an object to an opening in a body wall, comprising:
   an elongated tube defined by an inner and outer surface and having a proximal end and a distal end;
   at least one gripping member formed to store a force when in a restrained position, attached to the outer surface of said tube;
   a sleeve slidably mounted over said tube, wherein said gripping member is restrained when said sleeve is in a first position and said gripping member is unrestrained when said sleeve is in a second position, releasing said stored force, allowing said gripping member to move toward the body wall.

2. The apparatus of claim 1, wherein said gripping member expands outwardly from said tube when unrestrained by said sleeve.

3. The apparatus of claim 2, wherein said gripping member applies a compressive force to the inner body wall around the opening.

4. The apparatus of claim 3, further comprising:
pad means mounted on said member for distributing the compressive force to the body wall exerted by said gripping member when said sleeve is in said second position.

5. The apparatus of claim 1, wherein said sleeve extends through the opening to reduce damage to the body tissue.

6. The apparatus of claim 1, wherein said tube is further defined by at least one slot.

7. The apparatus of claim 6, wherein said at least one gripping member is at least partially inset in said slot when said sleeve is in said first position.

8. A fixation apparatus to hold an object to a body opening, said body opening having an inner and outer body wall, comprising:
an elongated tube defined by an inner and outer surface and having a proximal end and a distal end, wherein said tube has at least one slot;
at least one outwardly biased member attached to the outer surface of said tube, wherein said member selectively applies a force to the body wall;
a sleeve slidably mounted over said tube, wherein said at least one member is restrained at least in part in said slot and against said outward bias when said sleeve is in a first position and said member is unrestrained, allowing said outward bias to move said member toward a body wall when said sleeve is in a second position.

9. The apparatus of claim 8, further comprising:
means mounted on said tube to facilitate positioning of said sleeve on said tube; and
means for capturing the outer body wall, movably mounted on said sleeve, wherein said means can be positioned on said sleeve to apply an inward force to the body wall in opposition to said member.

10. The apparatus of claim 8, further comprising pad means mounted on said member for distributing said force to the body wall exerted by said member when said sleeve is in said second position.

11. The apparatus of claim 10, wherein said pad means is substantially flush with said sleeve when said sleeve is in said first position.

12. The apparatus of claim 8, wherein said sleeve extends through the opening to reduce damage to the body tissue.

13. A method for securing an object to an opening in a body wall, comprising the steps of:
restraining at least one member against a tube in a manner where the restraint causes potential energy to be stored in the member;
inserting the tube into the opening; and
releasing said member to allow the potential energy in said member to be converted to kinetic energy to expand the member outwardly.

14. The method of claim 13, wherein the step of restraining is accomplished by:
positioning a sleeve adjacent the member; and
uncoiling the member.

15. The method of claim 14, wherein the step of releasing is accomplished by:
sliding said sleeve along said tube to a position adjacent the proximal end of said tube; and
allowing the member to coil into contact with the body wall to apply a load to the body wall.

16. The method of claim 13, further comprising the step of applying an inward compressive force to the outer body wall around said opening.

17. The method of claim 16, wherein the step of applying an inward compressive force is accomplished by moving a stop along said sleeve to a position adjacent the outer body wall.

18. The method of claim 15, wherein the step of allowing is further accomplished by distributing the load applied by the member.

19. A fixation apparatus to hold an object to an opening in a body wall, comprising:
an elongated tube defined by an inner and an outer surface and having a proximal end and a distal end;
at least one member to selectively apply a force to the body wall, attached to said tube; and
said member further comprising pad means for distributing said force to the body wall, operable in at least two positions, wherein said pad means is substantially flush with said tube in a first position and said pad means selectively expands outwardly in a second position.

20. The apparatus of claim 19, wherein said member further comprises:
said member shaped to store a force, wherein said element is outwardly biased due to its shape;
a sleeve slidably mounted over said tube, wherein said member is restrained when said sleeve is in a first position and said member is unrestrained when said sleeve is in a second position.

21. The apparatus of claim 19, wherein said member expands outwardly from said tube when unrestrained by said sleeve.

22. The apparatus of claim 19, wherein:
said tube has at least one slot; and
said member mounted at least in part in said slot when restrained by said sleeve.

* * * * *